United States Patent [19]

Cottone, Jr. et al.

[11] Patent Number: 5,251,638
[45] Date of Patent: Oct. 12, 1993

[54] BIOPSY FORCEPS DEVICE HAVING IMPROVED HANDLE ASSEMBLY

[75] Inventors: Robert J. Cottone, Jr., Fort Lauderdale, Fla.; Joseph J. Kopp, Jr., Atlanta; David S. Rowley, Smyrna, both of Ga.

[73] Assignee: Cordis Corporation, Miami, Fla.

[21] Appl. No.: 869,379

[22] Filed: Apr. 16, 1992

[51] Int. Cl.⁵ ............................................. A61B 10/00
[52] U.S. Cl. ................................... 128/751; 606/206
[58] Field of Search ............... 128/751, 749; 606/167, 606/170, 171, 174, 205, 206, 207, 208

[56] References Cited

U.S. PATENT DOCUMENTS

| | | | |
|---|---|---|---|
| 3,964,468 | 6/1976 | Schulz | 606/171 |
| 4,815,476 | 3/1989 | Clossick | 128/751 |
| 4,887,612 | 12/1989 | Esser et al. | 128/751 |
| 5,074,311 | 12/1991 | Hasson | 128/754 |
| 5,147,380 | 9/1992 | Hernandez et al. | 606/207 |

Primary Examiner—Max Hindenburg
Assistant Examiner—Guy V. Tucker
Attorney, Agent, or Firm—Tarolli, Sundheim & Covell

[57] ABSTRACT

A biopsy forceps device is presented herein which employs a forceps assembly having a pair of forceps connected to the distal end of a control wire having its proximal end extending into a hub. A control wire actuator is connected to the proximal end of the control wire and the actuator is slidably mounted to the hub for slidable movement relative thereto between proximal and distal positions for respectively causing the forceps to be in a closed condition and in an open condition. A releasable locking mechanism normally blocks forward slidable movement of the actuator to prevent the forceps from being actuated to an open condition. A release mechanism releases the locking means from blocking forward movement of the actuator to thereby permit forward movement of the actuator causing the forceps to be actuated to an open condition.

6 Claims, 5 Drawing Sheets

BIOPSY FORCEPS DEVICE HAVING IMPROVED HANDLE ASSEMBLY

FIELD OF THE INVENTION

The present invention relates to biopsy forceps and, more particularly, to an improved biopsy forceps device having an improved handle assembly.

DESCRIPTION OF THE PRIOR ART

Biopsy forceps are known in the art and are in wide use for purposes of obtaining a tissue sample. One example of the prior art takes the form of the J. P. Clossick U.S. Pat. No. 4,815,476, assigned to the same assignee as the present invention. Such a forceps device includes a handle assembly slidably mounting a trigger member thereon and an elongated coil spring guide connected to the handle assembly at the proximal end of the guide. A pair of forceps are mounted to the distal end of the guide and a stylet-control wire received within the lumen of the guide is connected at its proximal end to the trigger and at its distal end to the pair of forceps.

A guide sheath may be introduced into a patient's body vessel, such as an artery, and the distal end of the forceps device is introduced into the sheath and guided to the site of interest. The handle assembly remains outside of the patient's body allowing the attending physician to operate the trigger. Forward movement of the trigger causes the stylet-control wire to move the forceps to an open position and rearward movement of the trigger causes the pair of forceps to move to a closed position to capture a tissue sample therebetween. The forceps device is then removed from the guide sheath so that the captured tissue sample may be examined.

The handle assembly employed in the Clossick patent discussed above is sometimes referred to as a syringe-type handle in that it includes a figure eight double finger trigger slidably mounted on the handle portion. The handle portion has a thumb ring at one end thereof. This requires the attending physician to put his thumb in the thumb ring and grasp the trigger with two fingers to achieve slidable movement of the figure-eight trigger relative to the thumb ring when actuating the forceps between open and closed positions. The handle is grasped by a physician while attempting to remove captured tissue from a body vessel and has, in practice, been found somewhat uncomfortable to many physicians requiring modifications to the handle, such as a flexible coupling permitting angular pivotal movement of the handle during such operation.

Another example of a prior art biopsy forceps device takes the form of the W. P. Schulz U.S. Pat. No. 3,964,468. The device disclosed in that patent includes a scissor-like handle design wherein a pair of tong legs are hinged together by a pin. At one end of each leg there is provided a finger grip or a thumb grip so that the physician may operate the scissor-like structure with a thumb and one finger on one hand. The distal end of one leg is connected to the proximal end of a control wire and the distal end of the other leg is connected to a flexible catheter including an elongated coil wire guide. The control wire extends through the lumen in the wire guide. The distal end of the control wire is connected to a forceps assembly. The attending physician may grasp this scissor-like structure with a thumb and a finger of one hand and by manipulating the scissor legs toward and away from each other, the control wire may be advanced and retracted to open and close the forceps assembly. The patent to Schulz, while disclosing a scissor-like handle assembly for use with a biopsy forceps device, does not provide locking means for normally locking the control wire in a forceps closed position by blocking movement of the control wire in a forward direction to open the forceps together with a means for releasing such a locking means.

SUMMARY OF THE INVENTION

In accordance with the present invention, there is provided a biopsy forceps device having a handle assembly employing an elongated central hub having distal and proximal ends. A forceps assembly is provided and it includes a pair of forceps. A control wire having proximal and distal ends is coupled at its distal end to the forceps assembly. A control wire actuator is connected to the proximal end of the control wire and the actuator is slidably mounted to the elongated central hub for slidable movement relative thereto between a proximal position and a distal position for respectively causing the forceps to be in a closed condition and in an open condition. Releasable forceps locking means normally locks the forceps in a closed condition and serves to normally block forward slidable movement of the actuator when the actuator is in its proximal position to thereby prevent the forceps from being actuated to an open condition. Release means are provided for releasing the locking means from blocking forward movement of the actuator to thereby permit forward movement of the actuator to cause the forceps to be actuated to an open condition.

In accordance with a still further aspect of the present invention, the handle assembly includes a pair of scissor-like wing members each pivotally mounted to the distal end of the central hub member and wherein the wing members include camming means for engaging the control wire actuator and displacing same in a proximal direction while closing the forceps.

BRIEF DESCRIPTION OF THE DRAWINGS

The foregoing and other objects of the invention will become more readily apparent from the following description of the preferred embodiment of the invention as taken in conjunction with the accompanying drawings which are a part hereof and wherein.

DESCRIPTION OF THE PREFERRED EMBODIMENT

Figure 1:
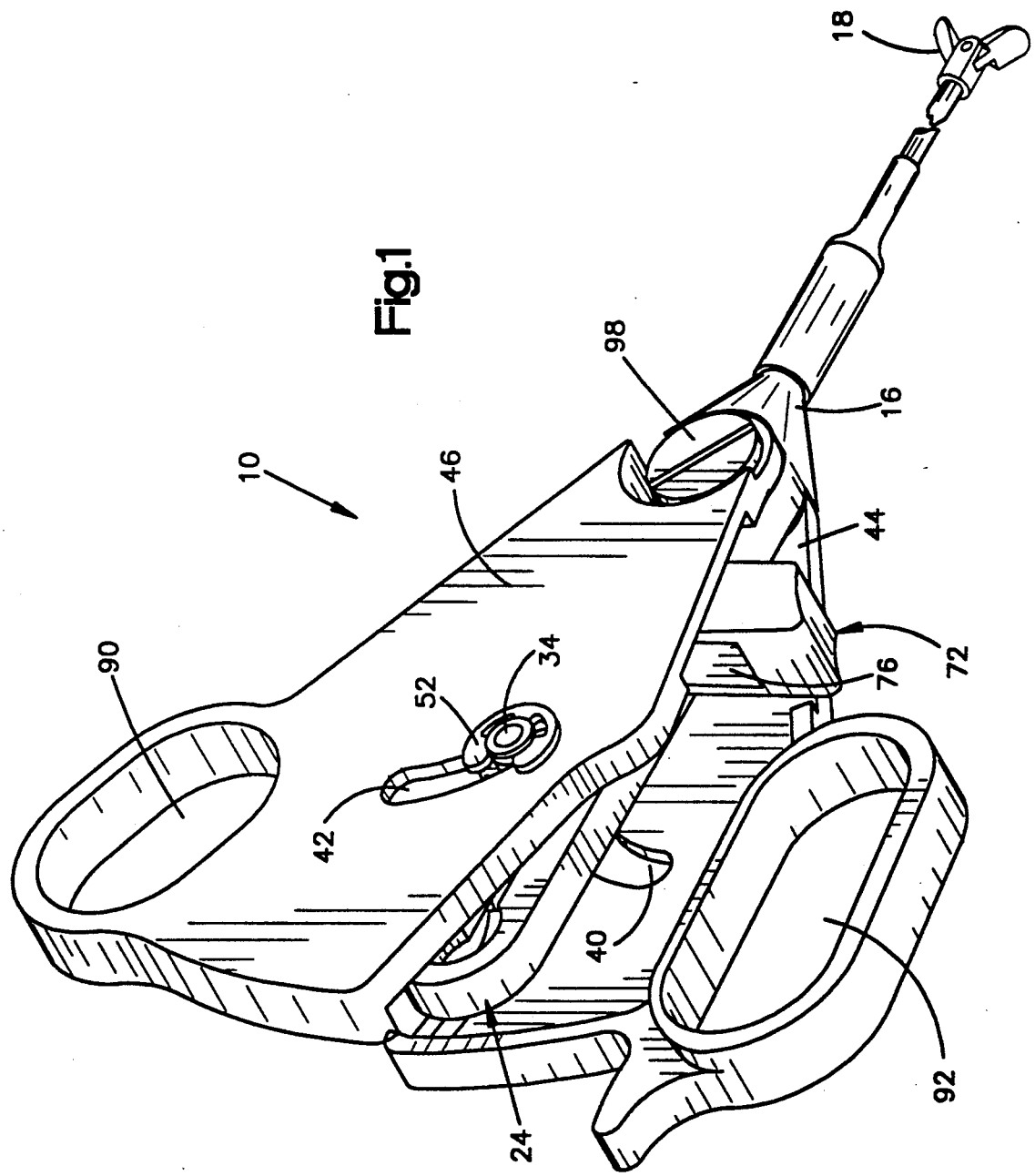
FIG. 1 is a perspective view of a biopsy forceps device constructed in accordance with the present invention.

Reference is now made to the drawings wherein the showings are for purposes of illustrating a preferred embodiment only and not for purposes of limiting same.

As shown in the drawings, there is provided a biopsy forceps device 10 which includes a handle assembly 12 and an elongated flexible hollow body taking the form of a coil spring guide 14 (see FIG. 3) which extends from the distal end 16 of the handle assembly to a forceps assembly 18. The guide 14 has a lumen extending throughout its length and the lumen slidably receives a control wire 20 which is connected at its distal end to the forceps assembly 18 and at its proximal end extends into the handle assembly 12 and is secured to a control wire actuator 22 slidably carried by a central hub 24 located within the handle assembly 10. The actuator 22 is provided with a passageway which receives a portion of the length of control wire 20 at the proximal end thereof and is secured thereto as with a suitable set screw arrangement, not shown.

The control wire actuator includes a central barrel-shaped portion 23 extending between a pair of cam lobes 26 and 28, each of which has a flattened portion 30 (see FIG. 3) for locking purposes, to be described hereinafter. Extending transversely outward from cam lobes 26 and 28 are cam followers 32 and 34, respectively. Cam followers 32 and 34 extend through arcuate shaped cam tracks 40 and 42. Cam tracks 40 and 42 are slots and are respectively located in a grip wing 44 and a thumb wing 46 which are pivotally mounted to the central hub 24 near its distal end. The cam followers 32 and 34 are held in place by means of spring lock washers 50 and 52 which fit over the ends of cam followers 32 and 34 and are locked in place in suitable annular grooves provided in the cam followers.

Figure 3:
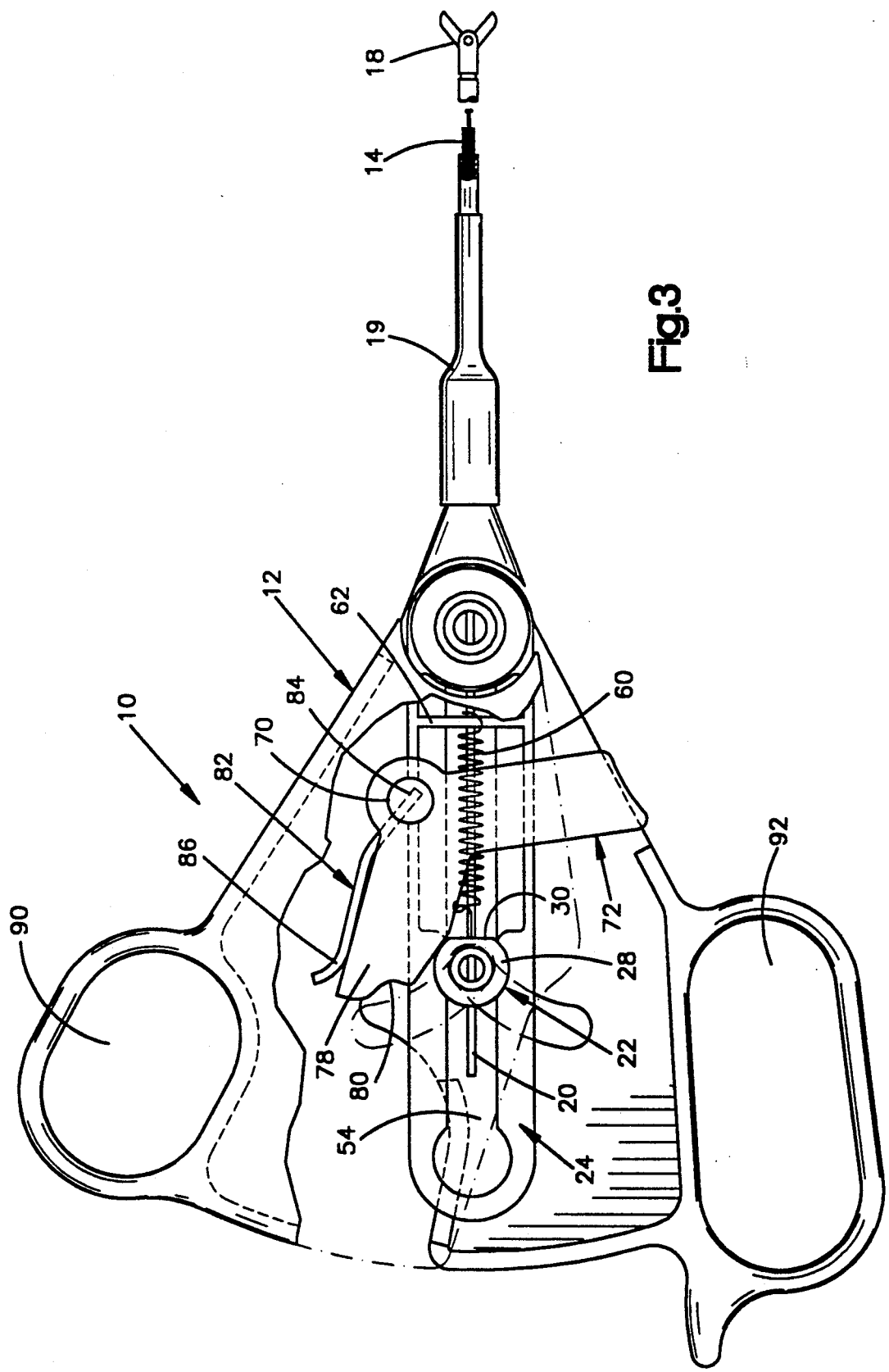
FIG. 3 is a view partly in section, of the device illustrated in FIGS. 1 and 2, with the scissor wings spread apart to a forceps open condition.
Figure 5:
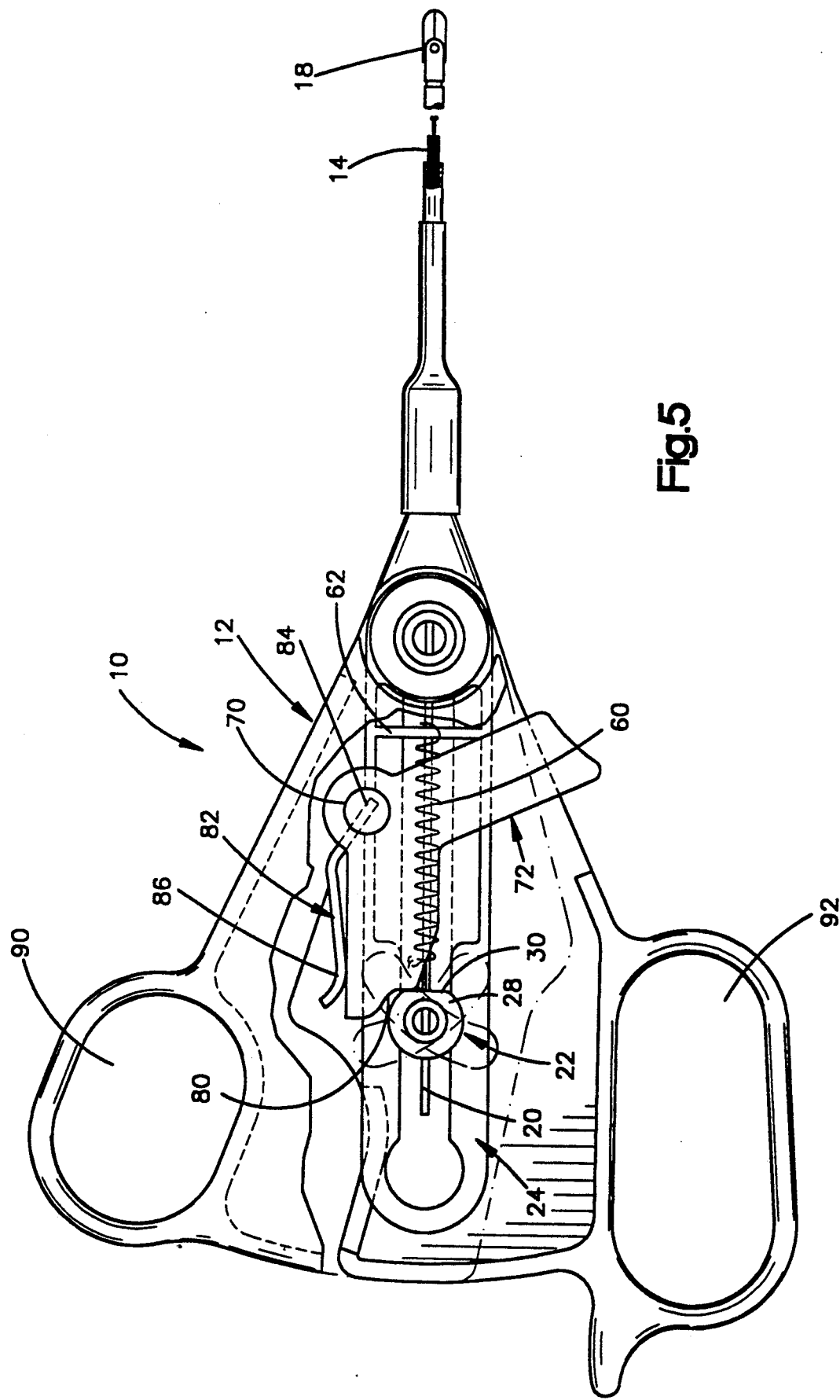
FIG. 5 is a view similar to that of FIG. 4, but showing a locking pawl blocking forward movement of the control wire actuator to prevent the forceps from being actuated to a forceps open condition.

The central barrel portion 23 of the actuator 22 is slidably received within an elongated track or slot 54 in the hub 24. The actuator 22 is mounted to the hub 24 for slidable movement within slot 54 between a proximal position, as shown in FIG. 5, and a distal position, as shown in FIG. 3. When the actuator is moved to its distal (or forward) position, it moves the control wire 20 in a distal direction to cause the forceps assembly to be in an open condition. When the actuator 22 is displaced to its proximal position (FIG. 5) the control wire is moved in a rearward or proximal direction to cause the forceps assembly 18 to be in a closed condition.

The actuator 22 is resiliently biased toward its distal position by means of a compression spring 60 which coaxially surrounds a portion of the length of the control wire 20 with the spring being suitably anchored at one end to the actuator 22 and at the other end to a crossbar member 62 on the central hub 24.

The central hub 24 also carries a pair of pivot posts 70 which extend transversely away from the hub. These pivot posts serve to pivotally carry a trigger 72 which is provided with a pair of holes 74 which receive the pivot posts 70 so that the trigger 72 may pivot about the pivot posts. The trigger 72 has a trigger leg 76 and a lock pawl leg 78. An exposed end of the trigger leg 76 is shown in the drawings with the exposed end being available to a physician by using his index finger to grasp the trigger leg and pivot it in a clockwise direction about the pivot posts 70. The pawl leg 78 includes a lock pawl 80 on its distal end and this lock pawl is configured to bear against the flat surface 30 on the ca lobes 26 and 28 carried by the actuator 22, when in the locking position shown in FIG. 5. As shown there, the flat surface 30 of each of the cam lobes 26 and 28 bears against the lock pawl 80 under the resilient force of spring 60 to thereby block forward slidable movement of the actuator along the slot 54.

A trigger spring 82, which is somewhat S-shaped in cross section, has one end 84 extending into the hub 24 as by a slot within the hub for receiving the end 84. The opposite end 86 of spring 82 is provided with a slight bend so that it bears against the lock pawl leg 78 of the trigger 72 to thereby provide a counterclockwise resilient force helping to hold the lock pawl 80 in locking engagement with cam lobes 26 and 28.

The physician may pull the trigger 72 by grasping the end of the trigger leg 76 with his index finger and pull backward to cause the trigger to rotate in a clockwise direction about pivot post 70 against the resilient force exerted by spring 82. This will cause the trigger to be rotated from the position as shown in FIG. 5 to that as shown in FIG. 3. This is sufficient for the lock pawl leg 78 to rotate by an amount to permit the actuator 22 to be driven by resilient forces from spring 60 from its proximal position to its distal position at which the forceps are open.

The handle assembly 12 also includes a pair of scissor-like elements including the grip wing 44 and the thumb wing 46 briefly discussed hereinbefore. As will be brought out below, these wings are employed by a physician for displacing the actuator 22 from its distal position to its proximal position for closing the forceps assembly. The thumb wing 46 includes a thumb opening 90 which is configured to easily receive the thumb of a physician. Similarly, the grip wing 44 is provided with an opening 92 for receiving various fingers of the physician.

The wings 44 and 46 are pivotally mounted to the central hub 24 at a location intermediate the slot 54 and the distal end 16. The hub is provided near its distal end with a pair of transversely extending pivot posts 94. Each of the wings 44 and 46 is provided with a pivot sleeve 96 having an internal diameter sufficient that each pivot sleeve 96 may encircle a pivot post 94 and rotate relative thereto. Each pivot post 94 has an internal threading 95 for making threaded engagement with the threaded portion of a screw 98. Each of the screws 98 serves to secure one of the wings 44 or 46 onto one of the pivot posts 94.

Figure 2:
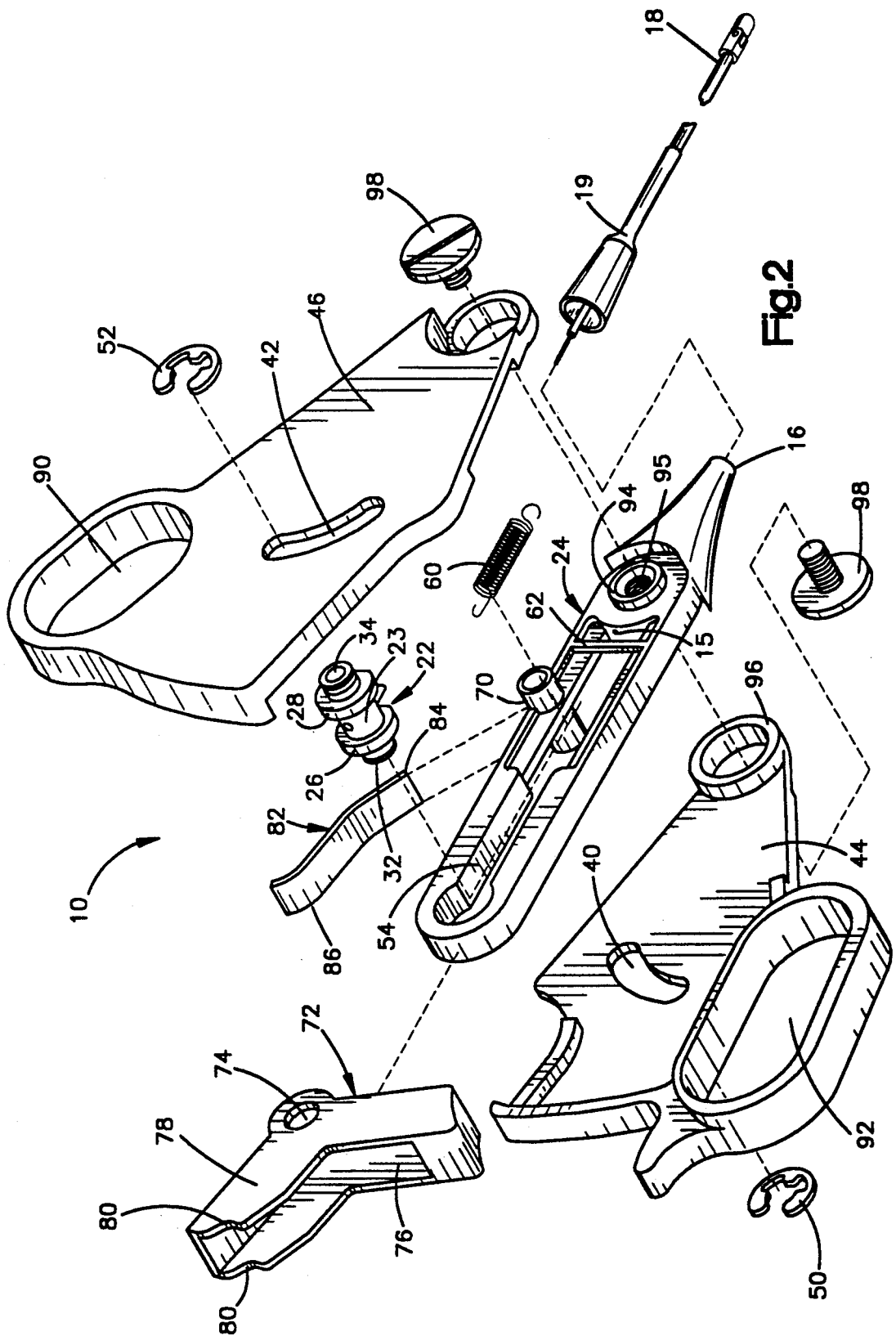
FIG. 2 is an exploded view showing various of the components employed in the embodiment illustrated in FIG. 1.

The distal end 16 of the hub has a lumen 15 which extends therethrough into the slot 54 of the hub 24. The lumen 15 is seen in FIG. 2. The lumen 15 permits movement of the control wire between its proximal and distal positions as the actuator 22 is displaced in slot 54. The screws 98 which hold the wings 44 and 46 in place are threaded toward each other, but do not meet, providing a space therebetween to accommodate a portion of the length of the control wire as it extends through the lumen 15 in the distal end of the hub. The coil spring guide 14 extends for a short distance into the lumen 15 at the distal end 16 of the hub and is held in place, as with a press fit. The protective sleeve 17 extends from the distal end of the hub to the forceps assembly 18. A protective plastic cap 19 extends over a portion of the length of sleeve 17 and the distal end 16 of the hub.

Figure 4:
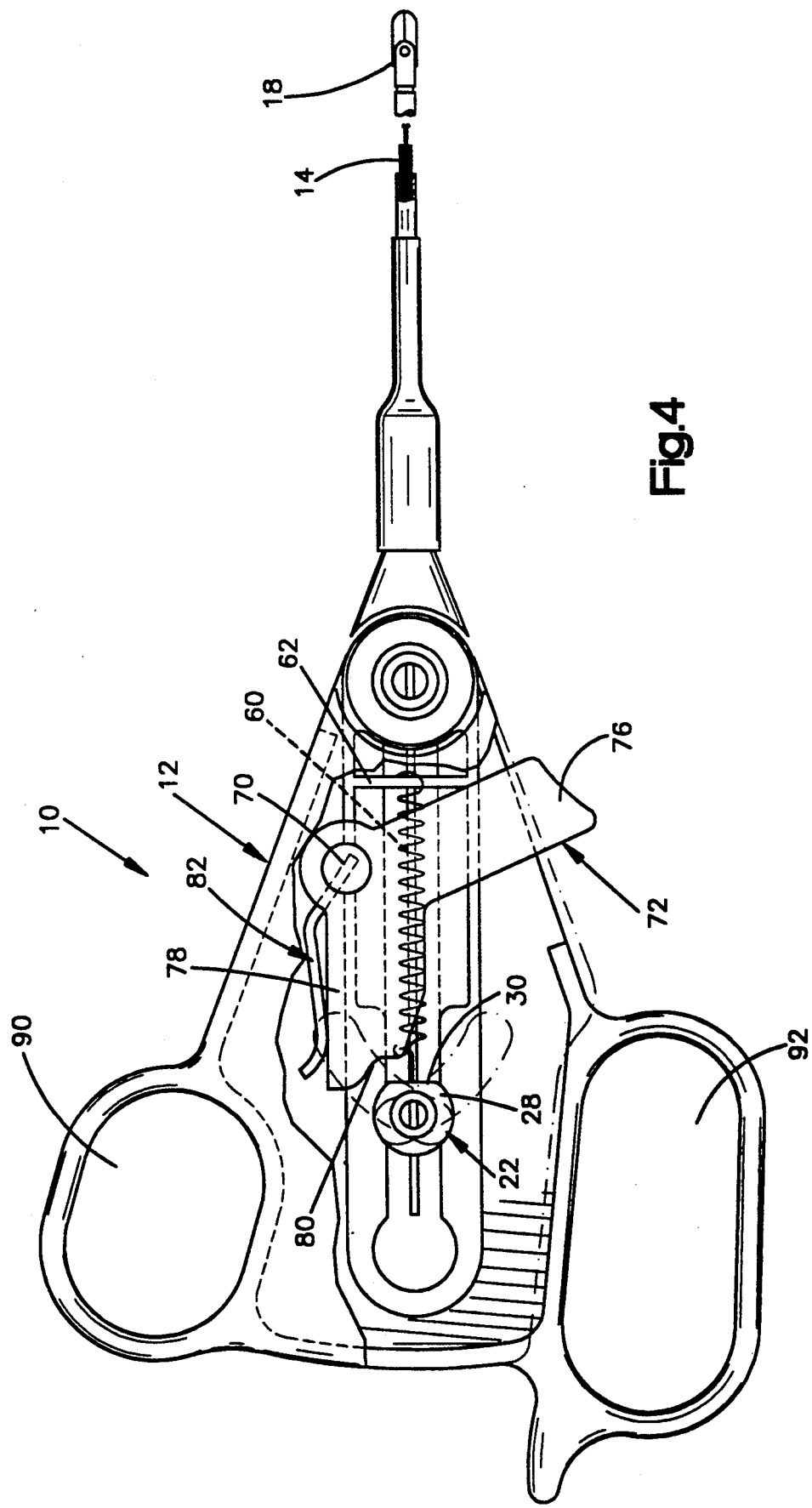
FIG. 4 is a view similar to that of FIG. 3, but with the scissor wings closed toward each other with the forceps in a closed condition.

The physician may grasp the handle 12 by placing his thumb through opening 90 and his index finger on the exposed end of the trigger leg 76 and inserting two other fingers through the opening 92 in wing 44. With the forceps initially in an open condition as shown in FIG. 3, the physician will now compress the two wings together from the condition as shown in FIG. 3 to that as shown in FIG. 4 and finally to a resting position as shown in FIG. 5. As the wings are compressed together, the cam tracks 40 and 42 cam against the cam followers 32 and 34 of the actuator 22. This causes the actuator 22 to be driven toward its full proximal position as shown in FIG. 4. During this movement, spring 82 resiliently biases the trigger 72 in a counterclockwise direction so that it rotates to the position as shown in FIG. 4 with the locking pawl 80 spaced from the cam lobes 26 and 28. As the physician now releases the compressive force on wings 44 and 46, the actuator 22 is pulled toward the lock paw 80 along slot 54 by means of the forces applied by spring 60 until the flat surface 30 of each cam lobe engages the locking paw. 80. This blocks forward sliding movement of the actuator to thereby maintain the forceps assembly locked in a closed condition as is shown in FIG. 5 even though the physician removes his hands and fingers from the handle assembly 12.

In summation, it is seen that the biopsy forceps device described hereinabove employs a scissor style handle which may be grasped by the physician in either hand. In operation the physician may place his thumb through the thumbhole 90 while resting his index finger on the exposed end of the trigger leg 76 and inserting at least some of his remaining fingers in the finger grip hole 92. If the forceps 18 are initially in a closed condition and locked in place, as is indicated by FIG. 5, the physician merely pulls back on the trigger leg 76 with his index finger. As the physician exerts force with his index finger on the exposed end of trigger leg 76, the trigger will pivot in a clockwise direction about pivot post 70 against the resisting force of spring 82. As the trigger pivots to a location as shown in FIG. 3, the actuator 22 is displaced under the force of spring 60 toward its distal position causing the forceps 18 to open.

The physician may now close the forceps by compressing the wings together so that the cam tracks 40 and 42 drive the actuator 22 toward its fully retracted position while the trigger 72 is pivoted in a counterclockwise direction under the force of spring 82 to the position as shown in FIG. 4. Thereafter, as the physician releases the compressive force on wings 44 and 46, the actuator 22 moves forward slightly until the flat surface 30 on cam lobes 26 and 28 engages the locking pawl 80 to lock the forceps in a closed condition.

Although the invention has been described in conjunction with a preferred embodiment, it is to be appreciated that various modifications may be made without departing from the spirit and scope of the invention as defined by the appended claims.

Having described the invention, the following is claimed:

1. A biopsy forceps device comprising:
   an elongated hub member having distal and proximal ends;
   an elongated flexible hollow body portion having a lumen extending therethrough and having a proximal end and a distal end;
   a forceps assembly coupled to the distal end of said body portion, and including a pair of forceps;
   a control wire having proximal and distal ends and extending through the lumen in said body portion and coupled at its said distal end to said forceps assembly;
   a control wire actuator connected to the proximal end of said control wire, said actuator being slidably mounted to said hub member for slidable movement relative thereto between a proximal position and a distal position for respectively causing said forceps to be in a closed condition and in an open condition;
   releasable forceps locking means for normally blocking forward slidable movement of said actuator when said actuator is in its said proximal position thereby preventing said forceps from being actuated to said open condition;
   said releasable forceps locking means includes means for displacing said locking means to unblock said locking means from preventing forward movement of said actuator means;
   said releasable forceps locking means includes a finger actuatable trigger pivotally mounted to said hub member for pivotal movement between a normal extended position whereby said actuator is blocked and a retracted position whereby said actuator is blocked and which may be actuated by an operator's finger from said normal extended position to said retracted position for causing said forceps assembly to be in its open position;
   means for resiliently biasing said actuator means toward its said distal position; and
   means for causing said forceps to be actuated to its closed condition.

2. A biopsy forceps device as set forth in claim 1 wherein said releasable forceps locking means includes a locking pawl carried by said trigger for normally blocking forward movement of said actuator means.

3. A biopsy forceps device as set forth in claim 1 wherein said means for causing includes means for slidably displacing said actuator on said hub member from said distal position to its said proximal position for causing said forceps assembly to be actuated to its said closed condition.

4. A biopsy forceps device as set forth in claim 3 wherein said hub member has an elongated guide track extending intermediate its proximal and distal ends, said actuator is slidably mounted to said guide track.

5. A biopsy forceps device as set forth in claim 4 wherein said means for displacing said actuator includes first and second wing members each pivotally mounted to said hub member at a location intermediate said track and said distal end of said hub member.

6. A biopsy forceps device as set forth in claim 5 wherein each of said wing members has a cam track in engagement with said actuator as said wing members are pivoted toward each other for causing displacement of said actuator toward its said proximal position.

* * * * *